(12) United States Patent
Calderon et al.

(10) Patent No.: US 11,978,542 B2
(45) Date of Patent: May 7, 2024

(54) ENABLING THE CENTRALIZATION OF MEDICAL DERIVED DATA FOR ARTIFICIAL INTELLIGENCE IMPLEMENTATIONS

(71) Applicant: Children's Hospital Los Angeles, Los Angeles, CA (US)

(72) Inventors: Fernando Yepes Calderon, North Hollywood, CA (US); James Gordon McComb, La Canada, CA (US)

(73) Assignee: CHILDREN'S HOSPITAL LOS ANGELES, Los Angeles, CA (US)

( * ) Notice: Subject to any disclaimer, the term of this patent is extended or adjusted under 35 U.S.C. 154(b) by 179 days.

(21) Appl. No.: 16/796,468

(22) Filed: Feb. 20, 2020

(65) Prior Publication Data

US 2020/0273551 A1    Aug. 27, 2020

Related U.S. Application Data

(60) Provisional application No. 62/808,651, filed on Feb. 21, 2019, provisional application No. 62/808,673, filed on Feb. 21, 2019.

(51) Int. Cl.
| | |
|---|---|
| G16H 30/20 | (2018.01) |
| G06F 16/248 | (2019.01) |
| G16H 15/00 | (2018.01) |
| G16H 30/40 | (2018.01) |
| G16H 50/20 | (2018.01) |
| G16H 50/30 | (2018.01) |
| G16H 70/20 | (2018.01) |
| H04L 67/01 | (2022.01) |

(52) U.S. Cl.
CPC ............ *G16H 15/00* (2018.01); *G06F 16/248* (2019.01); *G16H 30/20* (2018.01); *G16H 30/40* (2018.01); *G16H 50/20* (2018.01); *G16H 50/30* (2018.01); *G16H 70/20* (2018.01); *H04L 67/01* (2022.05)

(58) Field of Classification Search
CPC ..................................................... G16H 50/30
See application file for complete search history.

(56) References Cited

U.S. PATENT DOCUMENTS

| | | | | |
|---|---|---|---|---|
| 9,801,562 | B1 * | 10/2017 | Host-Madsen | ...... A61B 5/7275 |
| 2003/0229520 | A1 * | 12/2003 | Wise | ..................... G16H 40/67 |
| | | | | 705/50 |

(Continued)

OTHER PUBLICATIONS

"MR Quantification of Cerebral Ventricular vol. Using a Semiautomated Algorithm"; Johnson et al.; AJNR 14:1373-1376; Nov./Dec. 1993 (Year: 1993).*

(Continued)

*Primary Examiner* — John A Pauls
(74) *Attorney, Agent, or Firm* — MANNAVA & KANG, P.C.

(57) ABSTRACT

A system having patient image processing capability and being in compliance with health insurance portability and accountability act including a N-server having a database, wherein the N-server receives patient data in a form of numerical values from at least one sender and wherein the patient data is converted into numerical values prior to being sent to the N-server. Additionally, the system includes one or more artificial intelligence program to analyze the data in the form of numerical values and detect patterns for a predefined abnormality.

6 Claims, 7 Drawing Sheets

(56) References Cited

U.S. PATENT DOCUMENTS

| | | | | |
|---|---|---|---|---|
| 2004/0172287 A1* | 9/2004 | O'Toole | ............... | G16H 10/60 705/2 |
| 2007/0036402 A1* | 2/2007 | Cahill | ............... | G06T 7/0012 382/128 |
| 2011/0110568 A1* | 5/2011 | Vesper | ............... | G06Q 10/10 382/128 |
| 2011/0179044 A1* | 7/2011 | Crum | ............... | G06F 18/22 707/E17.014 |
| 2013/0231552 A1* | 9/2013 | Grady | ............... | A61B 5/7267 600/410 |
| 2014/0214683 A1* | 7/2014 | Dominick | ............... | G16H 30/20 705/51 |
| 2015/0100787 A1* | 4/2015 | Westin | ............... | H04L 63/0414 713/168 |
| 2016/0199215 A1* | 7/2016 | Kopelman | ............... | A61F 5/566 128/848 |
| 2016/0267221 A1* | 9/2016 | Larcom | ............... | G16H 70/00 |
| 2017/0103525 A1* | 4/2017 | Hu | ............... | G06T 7/0012 |
| 2017/0235913 A1* | 8/2017 | Aly | ............... | G16H 30/40 705/2 |
| 2017/0277831 A1* | 9/2017 | Ruff | ............... | A61B 6/485 |
| 2019/0108912 A1* | 4/2019 | Spurlock, III | ............... | G16H 50/20 |
| 2020/0074214 A1* | 3/2020 | Boespflug | ............... | G06V 10/267 |
| 2020/0151871 A1* | 5/2020 | Putha | ............... | G06F 40/30 |
| 2020/0161005 A1* | 5/2020 | Lyman | ............... | G16H 40/20 |

OTHER PUBLICATIONS

"Automatically measuring brain ventricular volume within PACS using artificial intelligence"; Yepes-Calderon et al.; Plos One; Mar. 15, 2018 (Year: 2018).*

"DCM2NII Dicom to NIfTI conversion"; Rorden, Chris; (captured by the Internet Archive on Feb. 28, 2018) (Year: 2018).*

"Convert various image formats to NIfTI"; Chris Rorden (Year: 2022).*

"Assessment of Hydrocephalus in Children based on Digital Image Processing and Analysis"; Fabijanska et al.; 2014; (Year: 2014).*

* cited by examiner

| Resolution: | 0.46x0.46x4 | 0.46x0.46x5 |
| Vol (px): | 199474.0 | 117933.0 |
| Vol (mm3): | 171016.7 | 129592.7 |
| Vol (ml): | 171.0 | 129.6 |

Ventricles change: Reduction of 41.4 ml

ENABLING THE CENTRALIZATION OF MEDICAL DERIVED DATA FOR ARTIFICIAL INTELLIGENCE IMPLEMENTATIONS

RELATED APPLICATIONS

This application claims priority to U.S. Provisional Application No. 62/808,673, filed Feb. 21, 2019; and U.S. Provisional Application No. 62/808,651, filed Feb. 21, 2019, the entire disclosures of both are hereby incorporated by reference.

FIELD OF THE INVENTION

The present disclosure generally relates to a system including a picture archiving and communication system including a server a database that is in communication with a process application system including a server and a database. The system can have patient image processing capability and can be in compliance with health insurance portability and accountability act. The system can include a numeric data collector that can convert patient data into a numerical value.

BACKGROUND OF THE INVENTION

A picture archiving and communication system (PACS) was designed to replace an old film archiving system used in hospitals to store and move various medical imaging modalities. PACS uses standard internet transport protocols and customized signaling to optimize image availability and assure good practices regarding confidentiality. PACS is ubiquitous in medical facilities, but lacks image-analytical capabilities.

Hospitals and clinics are augmenting the use of radiologic devices that assist clinicians in quantifying images in order to determine an accurate diagnosis. These devices yield numbers that are unintelligible when seen out of the clinical context and therefore, comply with the confidentiality regulations protected by the Health Insurance Portability and Accountability Act (HIPAA). Moreover, clinically-derived information is currently saved by hospitals without any other purpose than to adhere to ongoing legislation.

Developers have proposed different approaches to assert quantifications within PACS. These approaches range from building a new application from scratch to a full scheme of back-end and front-end plug-ins. The adoption of new systems is prohibitive because PACS is broadly used in hospitals (76% of the hospitals in the US in 2010). The plug-in options include limitations such as compatibility issues due to PACS architecture, which is closed. Additionally, the plug-in options are semi-automatic, which requires human input or interaction, which results in the entity using the plug-in not complying with the HIPAA regulations and requirements. The imaging tools that are designed to work inside the medical facilities must comply with the HIPAA or similar regulations around the world; therefore, semi-automatic procedures or strategies involving external material such as templates often preclude the implementation of analytical tools within PACS.

What is needed is a system that can perform unlimited analytical procedures without violating confidentiality policies or creating security breaches, and without perturbing the normal workflow of the PACS system. For example, a secure, small data flow system that can enable unlimited data processing capabilities with 3D rendering features without disturbing the operation of PACS or breaching any confidentiality regulations.

SUMMARY OF THE INVENTION

In an aspect, there is disclosed a system having patient image processing capability and being in compliance with health insurance portability and accountability act comprising: an N-server having a database, wherein the N-server receives patient data in a form of numerical values from at least one sender; wherein the patient data is converted into a numerical values prior to being sent to the N-server; and an artificial intelligence program in the N-server to analyze the data in the form of numerical values and detect patterns for a predefined abnormality.

In another aspect, there is disclosed a system including a processor; and a non-transitory machine-readable storage medium storing machine-readable instructions that are executable by the processor to: receive patient data in a form of numerical values from at least one sender, wherein the patient data is converted into numerical values prior to being sent to the N-server; analyze the data in the form of numerical values and detect patterns for a predefined abnormality, wherein based on the detected pattern anticipate at least one of probability of an event and a source of the cause of the determined pattern.

In an aspect, there is also disclosed A system having patient image processing comprising: a picture archiving and communication system (PACS) that runs on a client-server architecture and enables a user to share digital imaging and communications in medicine (DICOM) messages among stations; and a process application server (PAS) having access to DICOM, and incorporated in a local network.

In another aspect, there is disclosed A system comprising: a processor; and a non-transitory machine-readable storage medium storing machine-readable instructions that are executable by the processor to: generate a structured query that is forwarded to PACS; in response, receive a list of matched SOPs including a set of complying data from PACS; send a request to move the complying data corresponding to the matched SOPs; in response, receiving the complying data from PACS.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

BRIEF DESCRIPTION OF THE DRAWINGS

The present disclosure in its several aspects and embodiments can be more fully understood from the detailed description and the accompanying drawings, wherein.

Throughout this specification and figures like reference numbers identify like elements.

DETAILED DESCRIPTION OF THE INVENTION

Figure 1:
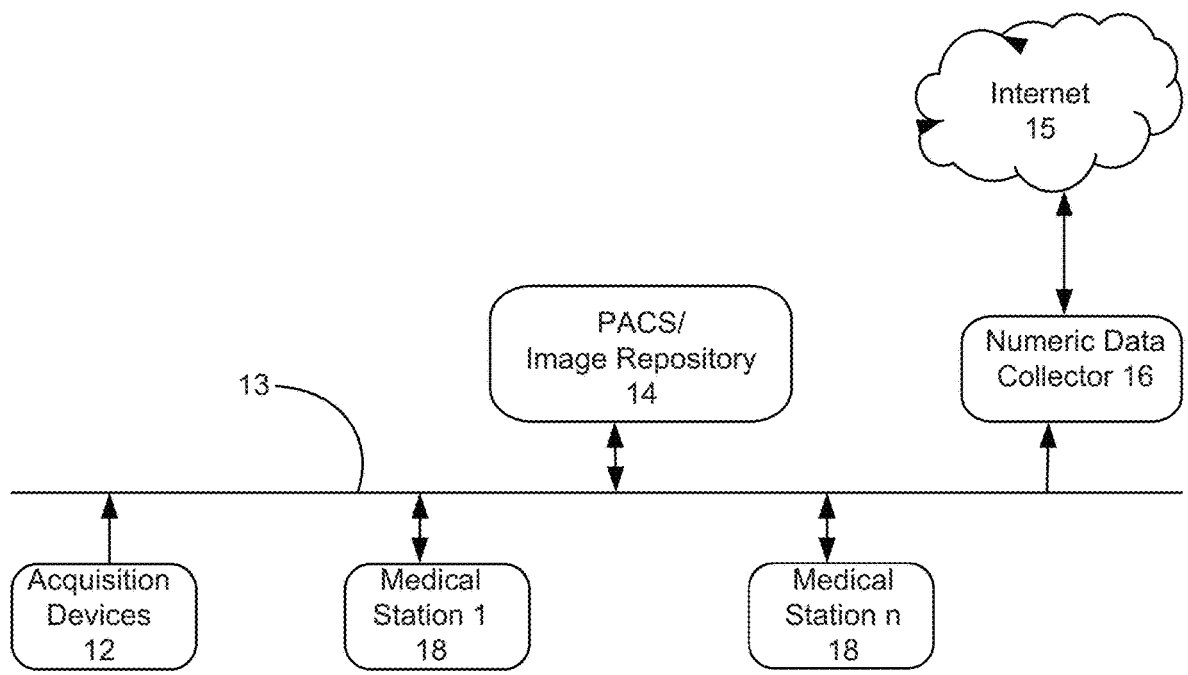
FIG. 1 is a work flow of a numeric data collector receiving raw data from various institutions, according to an example of the present disclosure.

It is to be understood that both the foregoing general description and the following detailed description are exemplary and explanatory only, and are intended to provide an explanation of various embodiments of the present teachings.

Clinically derived information is currently saved by hospitals without any other purpose than adhering to ongoing legislation and regulations, such as HIPAA. Thus, the gathered information is not being utilized to discover hidden patterns that can help specialist and medical professionals to make a more accurate diagnosis of a patient disorder.

This existing gathered data can be used at different levels of services depending on the number of institutions involved, the required data analysis, and the geographic area, among other things. For example, artificial intelligence (AI) can be used to facilitate work to be performed by medical specialists, how the needed data for the work to be performed is gathered among several institutions respecting confidentiality policies, and how to generate patient friendly reports and recommendations.

A system can collect data, convert the data to a number according to an algorithm, collect the numbers produced by the algorithm, and enable services based on AI. These services can include, but are not limited to, accurate and repeatable automatic diagnosis, reduction of intrusive procedures, such as biopsies, reduction of discrepancies among complex and life depending diagnosis, such as cancer, and recommending systems based on prediction assets. As the number of institutions participating in the data sharing increase, the database data can increase, which can increase the accuracy of the artificial intelligence (AI), classification, prediction, and conclusion. Additionally, this system can be HIPAA compliant given that the gathered data, which is converted to numbers, which are anonymized.

The system can enable picture archiving and communication system (PACS) to perform unlimited analytical procedures without violating confidentiality policies or creating security breaches, and without perturbing the normal workflow of the PACS system.

In an example, a secured transmission protocol, such as Secure Shell (SSH), can be used so that the system is not limited to only a single local institution, such as a clinic or hospital. When the communication between the system and the institution is established, the scope of the system grows to cover geographical regions that range from a block into a neighborhood, city, and worldwide level.

Even if each institution has its own proprietary architecture or a standard structure of files developed by a third party, the system of the present invention can be implemented. In an example, the communication between any computer with the capacity to produce numbers out of medical images or other medical resources can be accomplished by SSH tunneling, which can provide additional security when compared with standard Application Interfaces (API), such as the Representational State Transfer (REST). With the tunneling, the data can travel directly to a database of an internet-based server. The data can then be registered with a description of the context, a description of how the algorithm that produces the numbers work, the pathology, the meaning of each gathered feature, and the data span.

In an example, if access to different gadgets are provided to everyone, a host of standard procedures can be implemented to suit the final users' (the patients) needs, keeping the user updated on his/her medical information. This example suggests the incursion of medical applications to the one dollar market, where software gadgets are sold at a low cost, but to a broad audience. The initial applications can be focused on clinical and laboratory results. However, by involving a large number of institutions to collect a large quantity of data in a database, the database can be programmed to enable large population screening and monitoring. These predicting capabilities can result in reducing costs and resources and potentially move medicine more from a curative practice to a preventive practice.

In the system, a numeric data collector 16 can be used, as shown in FIG. 1, that is capable of converting raw data received from various institutions into numbers to prevent viewing of any private information and at the same time allow manipulation of the received data to create a desired report. In an example, the numeric data collector 16 can include a link 13 that can connect to one or more institutions with different data, which can be in various formats, and can convert the received data into numerical values. For example, an institution can include one or more of acquisition devices 12, PACS 14, and medical stations (1 through n, wherein n is an integer greater than 1) 18. Once the data has been received from one or more of these devices, the information can be converted into numerical values at numeric data collector 16 by, for example, a process application server (PAS). An example of how PAS can convert the collected information/data to numerical values is explained more fully below. For example, the PAS in the numerical data collector 16 can expand and decrypt the data received from the institutions, such as PACS 14, acquisition devices 12 or medical stations 18; anonymize the data, register the anonymized data, format the data, and process the data into numerical values. The numerical values can then be sent to a database via internet 15 using SSH tunneling for enhanced security.

Figure 2:
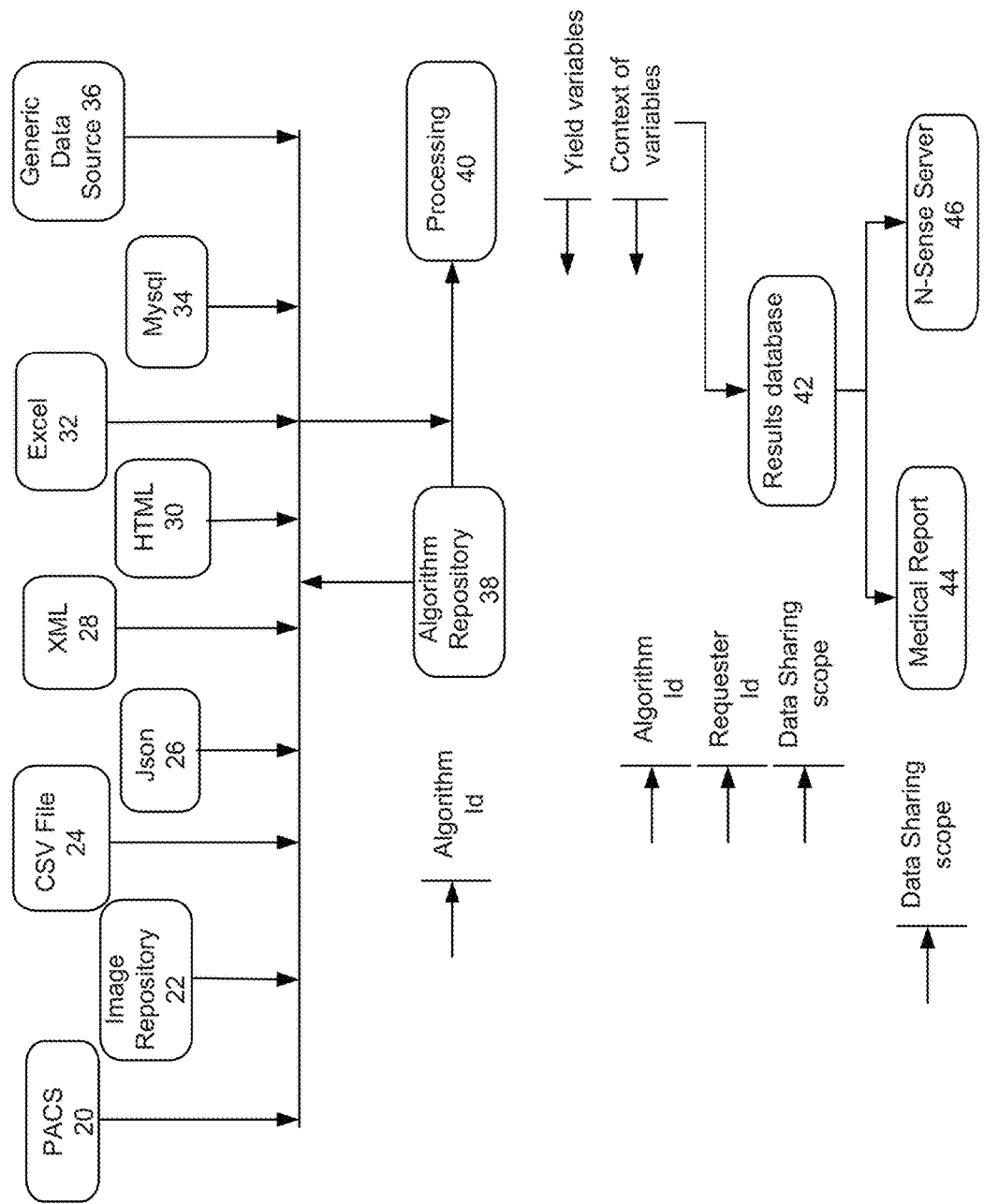
FIG. 2 is a work flow of the numeric data collector converting the raw data in various formats into numbers, according to an example of the present disclosure.

FIG. 2 illustrates a work flow of the numeric data collector 16, in which the received data from the institutions can be converted into numbers. As can be seen from FIG. 2, the data received by the numerical data collector 16 from the institutions, such as 12, 14, 18, can be in any format. For example, it can be in a digital imaging and communications in medicine (DICOM) format used by PACS 20, image repository format 22, CSV format 24, Json format 26, XML format 28, HTML format 30, Excel format 32, Mysql format 34, and/or generic data format 36. An algorithm 38 can be applied to the received data having different formats to process/convert 40 each set of data to a numerical value. Based upon input from a user, the system can process/convert the numerical value to a result that is stored in a database 42. The results can then be processed into a medical report 44 for a user, who can then review and use the report locally. Additionally, and/or alternatively, the result can be sent to a server 46 for use at a later time.

Figure 3:
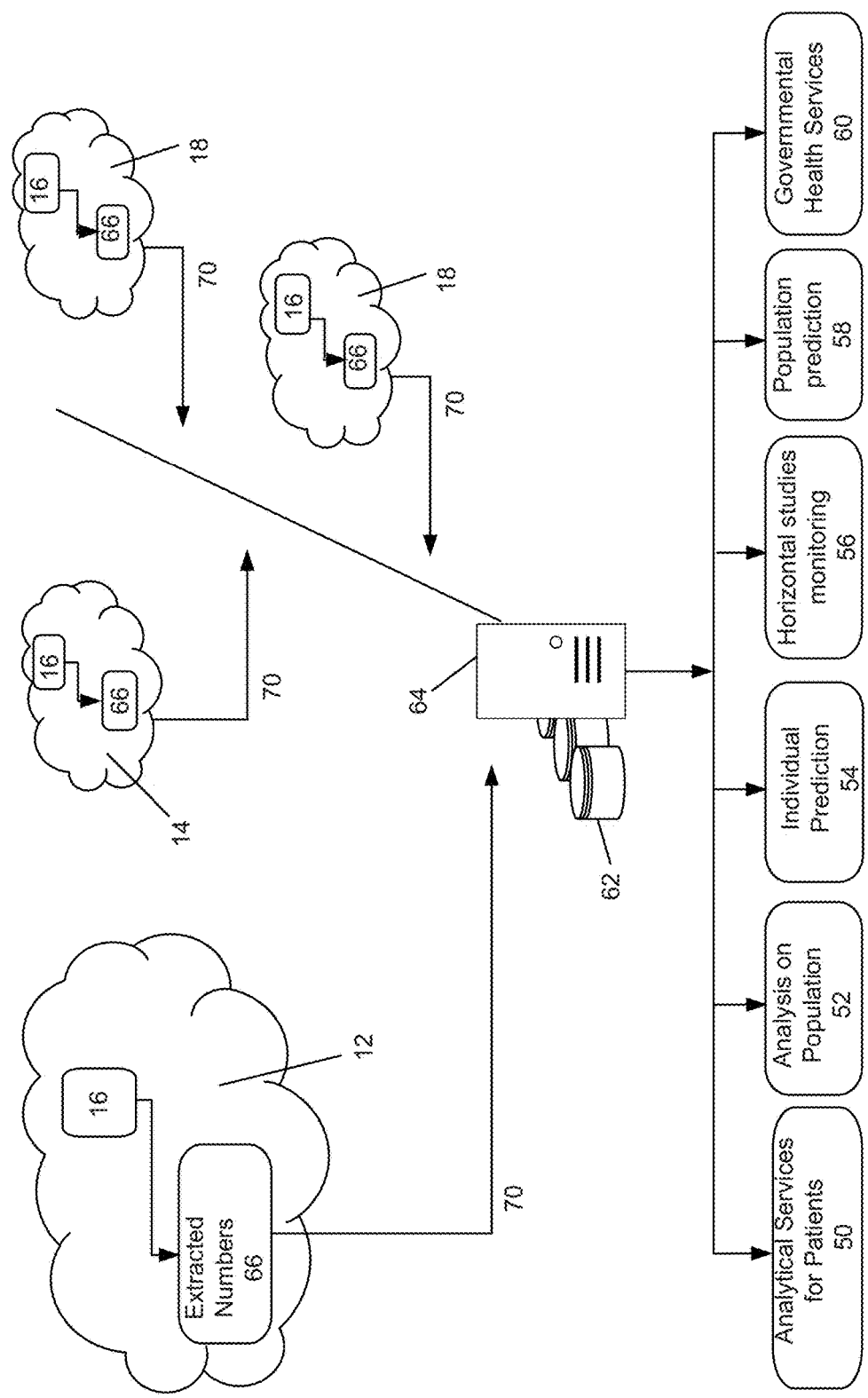
FIG. 3 illustrates a server that receives the collected numbers and processes the collected numbers, according to an example of the present disclosure.

Referring to FIG. 3, an overview of the system is illustrated. In an example, each institution 12, 14, and 18 can include a numeric data collector 16 and a number extractor 66. Once the numerical values have been generated by the numeric data collector 16, depending on the desired report or output, a set or a portion of the set of numbers generated by the numeric data collector 16 can be extracted by the number extractor 66. The extracted numerical values can then be sent to a central server 64 or cluster where the information can be saved in database 62. The saved information can then be used to conduct analytical services for patients at 50, analysis on a group of population in a predetermined geographical area at 52, predict potential issues with an individual in a predetermined area 54, conduct further studies on a certain population 56, predict the probability of a certain population developing a certain disorder 58, and/or provide information to governmental health services to determine a root cause of an outbreak 60.

EXAMPLE

Two institutions, one in LA and in San Diego were using an Automatic Ventricular Volume Estimator (AVVE). Using PACS-PAS system, each institution 18, used data from 30 patient cases for a total of 60 cases. The AVVE was used to calculate the volume of blood through each ventricle to determine which part of the ventricles was causing an abnormality.

The two institutions 18 executed a collaboration agreement to share the numbers gathered by the AVVE for each of their respective 30 cases and send them to an N-Server 46. An independent researcher ran an AI algorithm that checked the number values area by area of each patient and discovered a pattern. Kids in a first geographical location had dilatation of the brain ventricular region that went to the anterior part of the brain, while the ventricular growing pattern was more uniform in the second geographical area. Thus, the independent researcher concluded and confirmed by the AI that the dilatation happens with iso-pressure (pressure is the same in all directions) in the patients of the second institution 18. As the frontal part of the brain is associated with the capacity to analyze, the consequences of different pressure in the anterior region of the brain may cause problems to discern in kids living in the first geographical area.

Figure 4:
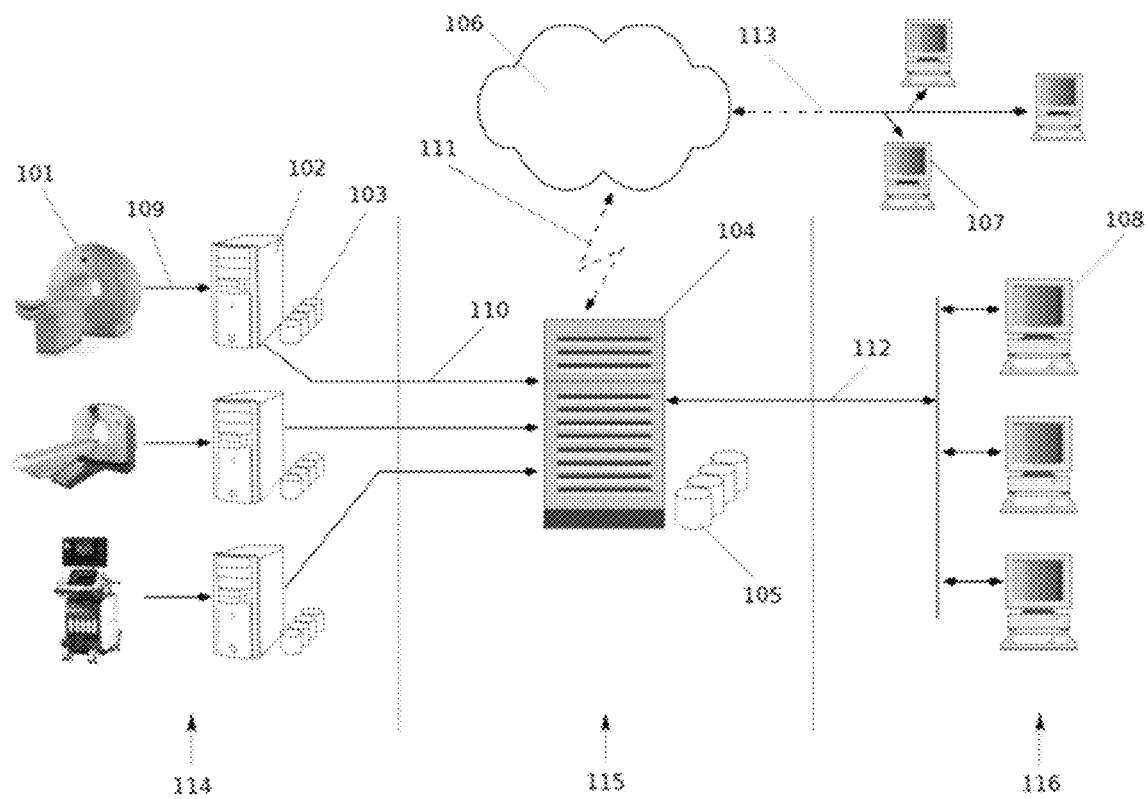
FIG. 4 illustrates the existing PACS that runs on a client-server architecture sharing DICOM messages among stations, according to an example of the present disclosure.

FIG. 4 illustrates a current PACS network, which can run on a client-server architecture sharing DICOM messages among stations. The medical images inside an institution, such as a hospital, can reside in one of two environments: the acquisition machine(s) 114 or the PACS system 115. The acquisition machines 114 can each include one or more acquisition systems 101, terminals 102, and a local database 103. The acquisition systems 101 can be in communication with the terminals 102 by data flow 109. The PACS system 115 can include PACS server 104 and database 105. Each of the terminals 102 can be connected to PACS system 115 by flow 110. Once the information is in the PACS server 104, the data can be made available for visualization through the viewers in environment 116. The environment 116 can include local clients 108 and optionally remote clients 107. The local clients 108 can be in communication with PACS server 104 via data flow 112. The optionally remote clients 107 can be in communication with PACS server 104 via data flow 111 through an internet cloud 106.

In an example, each of the acquisition systems 101 can temporarily store a set of files in their respectively associated terminals 102 that holds the local database 103. The data flow 109, are primarily raw data in native graphical formats including, but not limited to CSV 24, Json 26, XML 28, HTML 30, Excel 32, Mysql 34, JPG, TIFF, and PNG or PDF, reports that can be subsequently dicomized. The PACS server 104 can receive information holding DICOM headers, formerly called dicomized data. Information in the flow 110 can be dicomized. When the information in the flow 110 reaches PACS server 104, the DICOM fields can be read to create an entry profile in the database 105. When the information has been profiled in the PACS server 104, it is ready to be queried and visualized by the local clients' terminals 108. The local clients' terminals 108 can create the visual illustration of the information by creating a representation of the raw data without actually having access to the raw data. Remote clients 107, when authorized by the administrator, can also visualize the data. The data flow 112 can hold compressed/encrypted DICOM information that needs to be expanded/decrypted in the client's terminals 108 before the visualizers can render any information. Authorized clinicians can see the graphical representation of the data in their viewports, but they may not have access to the data at a bit level. This viewing access can be granted through a graphical user interface. Data flow 111, despite inherently being available in TCP/IP networks through cloud 106 (known as the internet), can generally be deactivated in PACS sever 104 due to security reasons, rendering data flow 113 void.

The PACS administrator can prevent the use of external scripts, but it does not necessarily restrict the routine functions of the client consoles. The PACS administrator's allowance of routine functions of the client consoles can allow the transformation of clients' terminals 108 into a PAS having at least a processor and a non-transitory machine-readable storage medium storing machine-readable instructions that can be executable by the processor. The PAS acquires the information using the same query/retrieve mechanisms utilized by any other authorized client on the network. However, unlike other clients' terminals 108, which can include a display to show the data to a user, PAS does not show any data to the user. Moreover, PAS has access to the data at a bit-level by handling raw data and keeping the source information in a numerical domain. Therefore, it has image-processing capabilities. Additionally, the PAS can create a variety of composite queries and intelligently move the created report by linking the report to one or several features recorded in the DICOM headers, e.g., "Bring all subjects diagnosed with severe hydrocephalus, younger than two months." In an example, PAS can convert the bit data (i.e., the numbers) into images and/or create other kinds of reports, such as converting the bit data into different domains. Although the end product can be forwarded to the user, the conversion of the bit data into a report, such as an image or any other representation resulting from an analytical method, is performed by PAS. Additionally, in some aspects, a user that has access to the generated report can be unable to convert the report back into its original bit data.

PAS can add more traffic to an already heavily used system. However, the PAS has enhanced filtering capabilities by accessing to all DICOM tags. With this level of access, a single image of a study can be retrieved for processing instead of requesting the whole study. The size of PAS-PACS transactions can be reduced by the querying method (C-Find instruction) that can be optimized to direct to specific instances within the studies, the transport method (C-Move instruction) that can be selective, transfer to be performed during network's low-traffic periods, and perform the anonymized entries in the PAS's storage so that there is no need for the information to be transferred twice for the same analytical procedure. All of these steps can be accomplished automatically without any human interaction so that the data and the entity in control of the data are in compliance with HIPAA.

PAS can receive compressed DICOM files, then uncompress these files and then pack them into Nifti format thereby facilitating the processing and anonymizing of the data. PAS can enhance visualization of the data linked to the proper study through the use of permalinks. The advantages of incorporating PAS into PACS architecture can be that PAS can move reports backward to the PACS. Such a move can be restricted to only dicomized-pdf reports.

Figure 5:
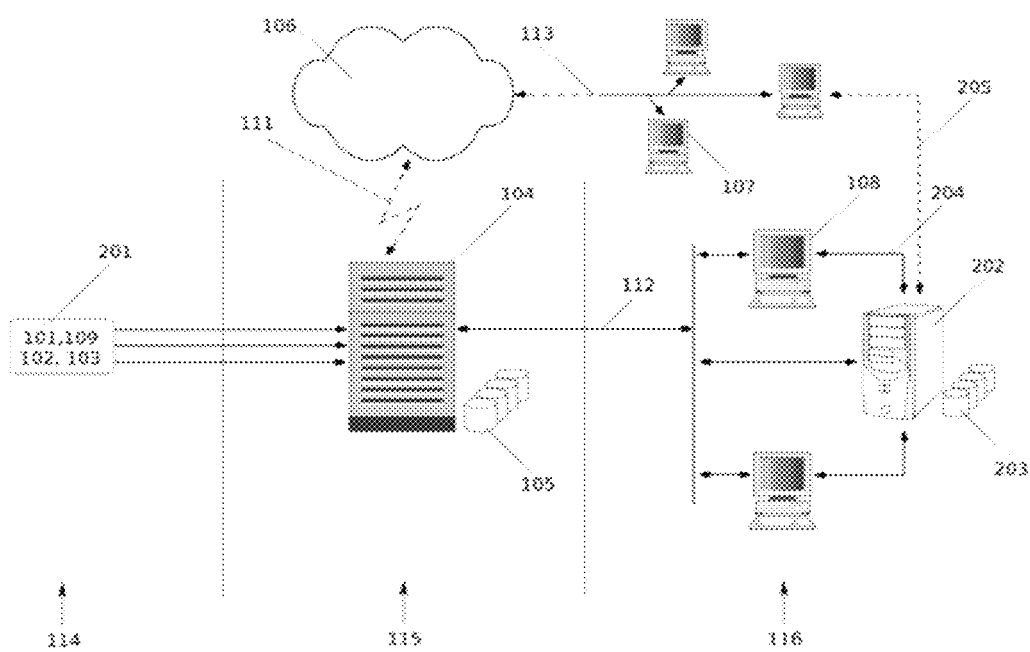
FIG. 5 illustrates the incorporation of a PAS into an existing PACS, according to an example of the present disclosure.

FIG. 5 illustrates an example of a PAS server 202 being incorporated into an existing system using PACS. In an example, a PAS server 202 includes database 203 in an institution, such as a hospital local network. As shown in FIG. 5, a PAS server 202 can be positioned on a client's terminal 108 side (i.e., it can be connected to the network as any other client). However, a PAS server 202 can also be located on a PACS sever 104 side, such as between the PACS server 104 side and the client's terminal 108, or anywhere else within the institution, such as a hospital local network.

PAS server 202 can acquire the information using the same querying mechanisms utilized by any other authorized client on the network. However, unlike other clients, the PAS server 202 has access to the data at a bit-level. Therefore, it is image-processing capable. The PAS server 202 can perform associative queries and retrieve data in a bulk manner. The PAS server 202 can be transparent to PACS administrators while its specifications enable the creation of innovative clinical and research-derived applications. With the PAS server 202 in the environment 116 network, new data flows 204 and 205 are created. Data flow 204 can be mainly used for loading the new analytical tools and for associating clinical studies or instances with analytical procedures. Data flow 205 can be kept optional, but if activated would provide to remote clients' terminals 107, the same services as the local clients' terminals 108.

Figure 6:
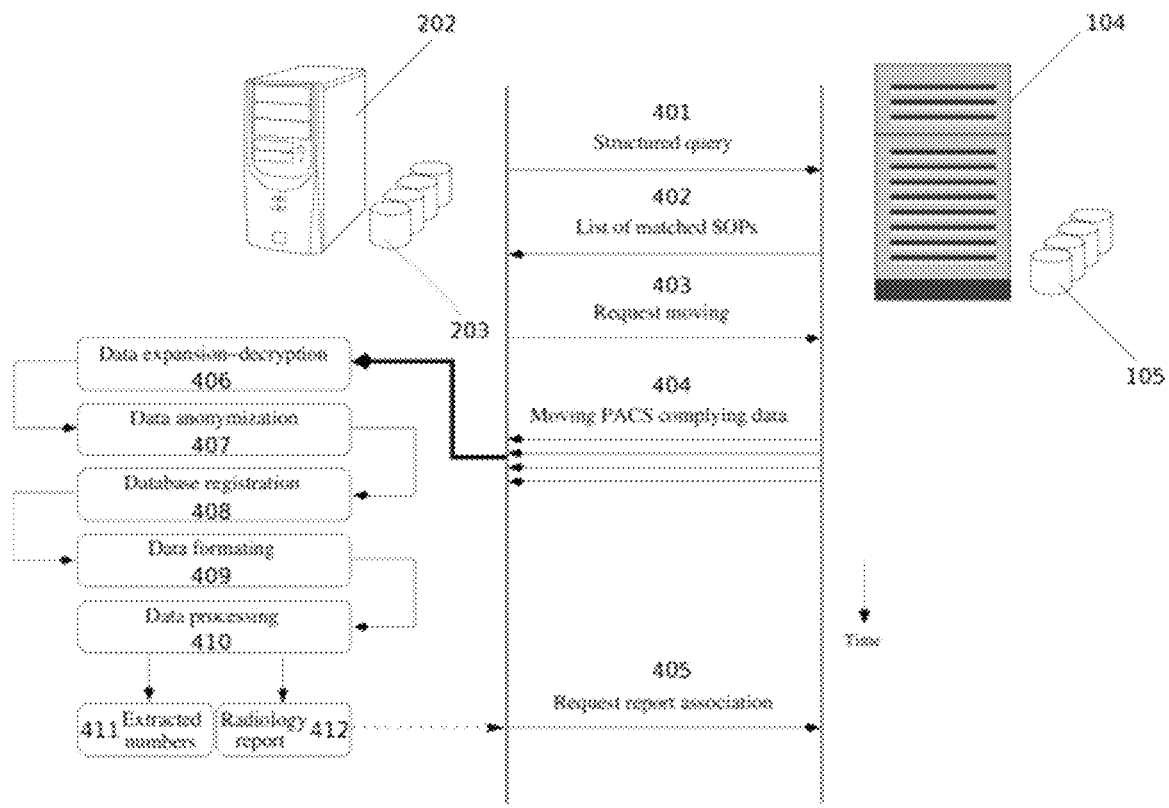
FIG. 6 illustrates PAS interactions and flow work in an enhanced PACS system, according to an example of the present disclosure.

In an example, when one of the local terminals 108 in the environment 116 network is converted to a PAS server 202 or if a PAS server 2020 is incorporated into the system, a new set of interactions can be enabled to create an enhanced PACS system. FIG. 6 illustrates PAS interactions and flow work in an enhanced PACS system and the new capabilities. Referring to FIG. 6, the left side corresponds to clients-PAS interactions and the PAS procedures. The horizontal column provides exemplary messages interchanged between the PAS server 202 and PACS server 104.

In the proposed architecture shown in FIG. 6, to operate the enhanced PAS system, a physician can be use a configuration interface 306 (FIG. 8) residing in a PAS server 202 to associate images of a study to corresponding procedures and to authenticate clinicians throughout a hypertext transfer protocol (HTTP).

The PAS server 202 can build a DICOM complying structured query 401, which can comply with the directives given by the user in a configuration interface 306. The PACS server 202 can respond by creating or generating a list of matched SOP 402 that include a set of complying data. Next, the PAS server 202 can issue a request to move/transfer 403 the set of complying data, and, in response, the PACS server 104 can start transferring the requested complying data 404.

In an example, the PAS server 202 can also schedule moving the complying data in low usage periods that can be dynamically defined by ping-tests. When the data transfer from the PACS server 104 to the PAS server 202 is complete, the PAS server 202 can proceed to decrypt and expand the data at 406, anonymize the data at 407 to scrub any potential personal information, and register the data in the PAS database at 408. In an example, only some of the information that is useful to reduce traffic and does not violate any confidentiality rules may be registered. Once registered, PAS server 202 can format or reformat the data at 409. The formatting can be done in a lighter format (e.g., Nifti, analyze).

After formatting 409, the data can be processed, by a numeric data collector 16, using a selected quantifying algorithm 410, which can generate a set of numbers that can be converted into a report. This quantifying algorithm 410 can generate numbers and can dissolve any ambiguities inherent of a qualitative domain, such as area, volume, thickness, curvature, depth, roughness, etc. by differentiating what is normal and what is considered to be abnormal by a specialist. This also can result in preventing use of vague language such as larger, smaller, deeper, etc.

The quantifying algorithms generate values that dissolve the ambiguities inherent of the qualitative domain. Those values refer to the area, volume, thickness, curvature, depth, roughness, spicularity and several other indexes built with mathematical methods around the concept that allows differentiation between what is normal and what is abnormal in the criteria of the specialists. Moreover, when the numbers are in place, comparisons abandon the vagueness present in statements such as bigger, smaller, deeper and so on, to create verdicts with exact numbers.

In an example, the generated set of numbers can be used to produce a desired report, such as a radiology image or report 412 that can be sent back to the PACS sever 104 via request report association 405. Additionally, or alternatively, the PAS server 202 can extract the set or a portion of the set of numbers at 411 from the results of the quantifying algorithm 410 and finally display the results using the extracted numbers at 411 at the user terminal 108. The set of numbers at 411 that are extracted from the result of running the qualifying algorithm at 410 in the numeric data collector 16 are such that no personal information can be derived from the numbers.

In an example, images of eight randomly selected children were chosen to feed the automatic maximum head circumference estimator (AHCE). Previously, the children underwent the standard head circumference measurement with a metric cloth tape, so the automatic process has a manual counterpart to estimate its accuracy. The clinical images have different acquisition parameters as those are chosen each time to favor patient comfort. The acquisition parameters for each patient are registered in Table 1 below.

TABLE 1

Comparison between manually and automatic obtained MHC using correction factors.

| Serial | Res | MHCE Manual | Automatic | Difference |
|---|---|---|---|---|
| 1 | 0.58 × 0.58 × 5.00 | 57.1 ± 0.1 | 57.6 ± 0.6 | −0.5 ± 0.6 |
| 2 | 0.41 × 0.41 × 4.00 | 44.8 ± 0.1 | 43.9 ± 0.5 | 0.9 ± 0.5 |
| 3 | 0.58 × 0.58 × 5.00 | 49.0 ± 0.1 | 49.6 ± 0.6 | −0.6 ± 0.6 |
| 4 | 0.85 × 0.85 × 3.99 | 48.5 ± 0.1 | 49.0 ± 0.6 | −0.5 ± 0.6 |
| 5 | 0.46 × 0.46 × 4.99 | 57.1 ± 0.1 | 56.4 ± 0.6 | 0.7 ± 0.6 |
| 6 | 0.57 × 0.57 × 4.99 | 54.6 ± 0.1 | 53.9 ± 0.6 | 0.7 ± 0.6 |
| 7 | 0.79 × 0.79 × 4.99 | 56.0 ± 0.1 | 55.5 ± 0.6 | 0.5 ± 0.6 |
| 8 | 0.57 × 0.57 × 4.00 | 42.2 ± 0.1 | 42.2 ± 0.5 | 0.0 ± 0.5 |

Figure 7:
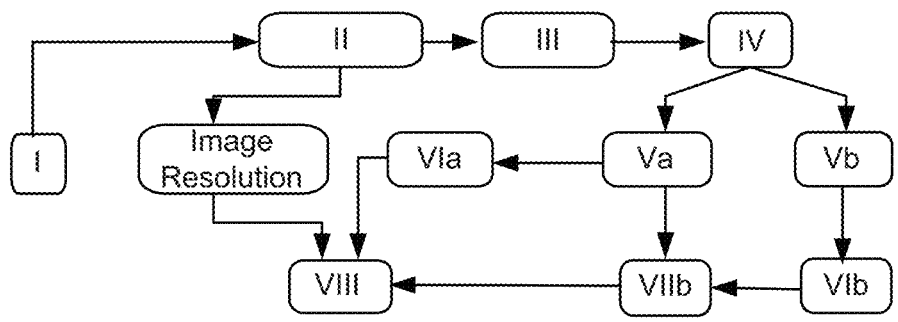
FIG. 7 is a pipeline for automatic maximum head circumference determination, according to an example of the present disclosure.

Referring to FIG. 7, in block I, the volumes of each head is extracted using the system shown in FIGS. 5 and 6. The extracted images undergo processing in block II to eliminate encryption, be uncompressed and set in a unified format different from DICOM. Next, at block III, the nypype module of python can be invoked to use an interface to FLS, which was created by Analysis Group at Oxford, UK and is a comprehensive library of analysis tools for FMRI, MM and DTI brain imaging data. At block IV, the FLS interface can be used to generate the surface of the head. From block IV, the masks corresponding to the out-skin, block Vb, and in-skull, block Va, segments are selected to continue the process. Here the pipeline is bifurcated. The first branch can be used to find the right location for MHC measurement that goes above the eyebrow level at block VIa. The second branch can detect the edges at block VIb. The edge can be detected by any method, such as by a CANI detector or by subtracting an eroded version of an image from its original image, and counts the number of pixels composing the outer edge of the skull, at block VIIb. Finally, the edge length can be calculated, at block VIII, as the product of the number of pixels in block VIIb and the pixel's length in the direction of propagation.

Figure 8:
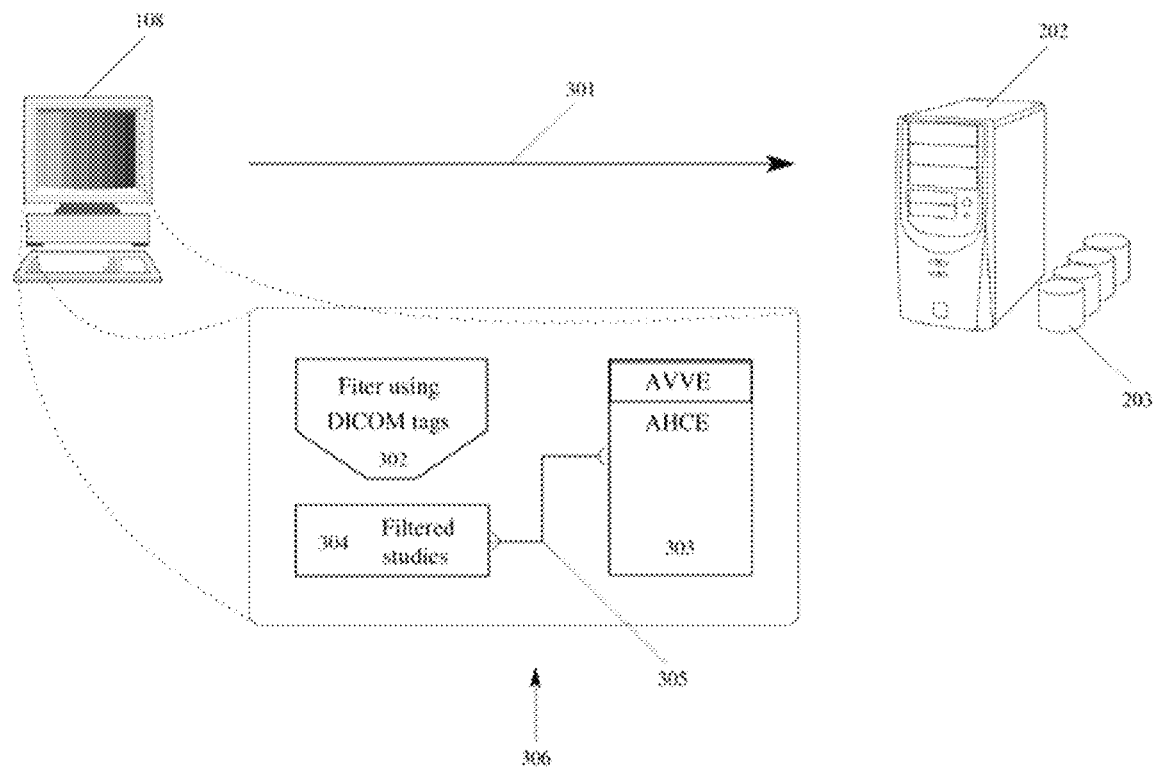
FIG. 8 illustrates a configuration interface of an enhanced PACS system, according to an example of the present disclosure.

FIG. 8 is an example of a PAS system having a configuration interface 306 that is visible in any client's terminal 108 of the institution, such as a local network, or remotely used client's interface 107, if allowed. The configuration interface 306 can include a data description selector, such as a filter using DICOM tag 302, an application selector/estimator 303, such as an automatic ventricular volume estimator (AVVE) and/or an AHCE, and a study selector, such as study filter 304.

Through the configuration interface 306, authorized users can set the PAS server 202 to execute quantifying procedures on the selected studies. The boosted querying capabilities of PAS can display extended filtering capabilities 304 where all DICOM labels are available 302; therefore, individual studies or populations can be selected.

Figure 9:
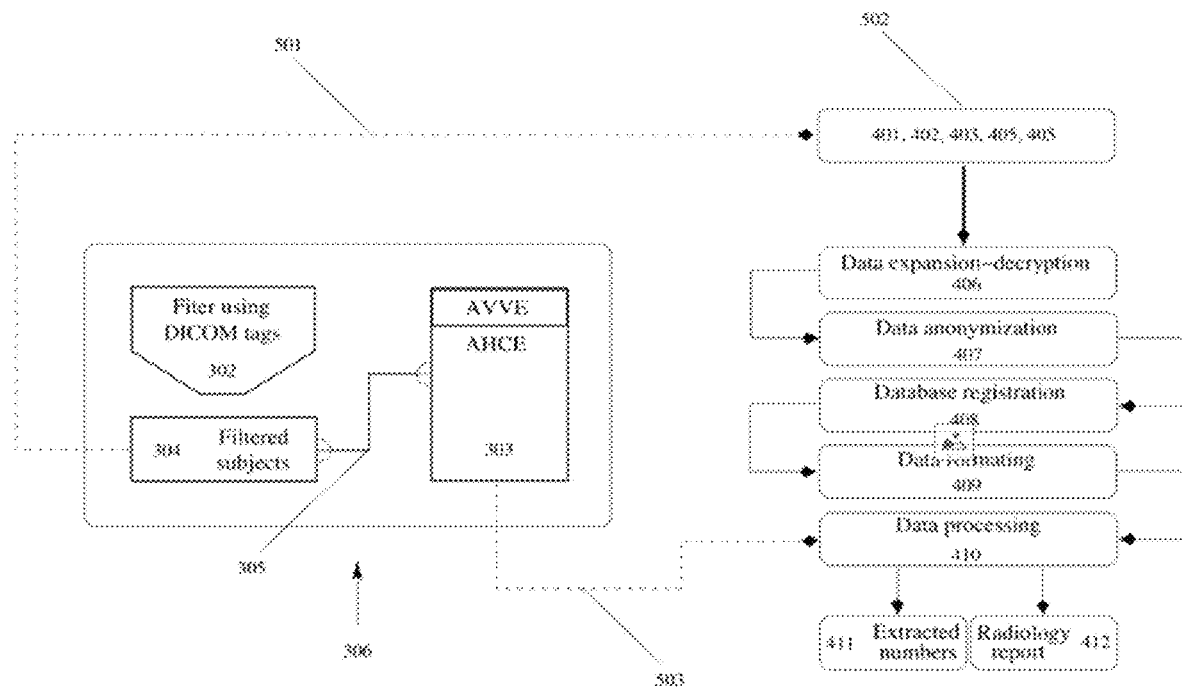
FIG. 9 illustrates the details of the interaction between a configuration interface and flow work in an enhanced PACS system, according to an example of the present disclosure.

In an example, as shown in FIG. 9, a plurality of links 305 can exist between the estimator 303 and the filtered subjects 304. Thus, a selected study can be associated with multiple quantifying procedures and a quantifying procedure can act over several studies.

The interaction details between the configuration interface 306 and flow work in an enhanced PACS system is illustrated in FIG. 9. When the data transfer from the PACS to the PAS is complete, the PAS server 202 proceeds to decrypt and expand at 406, anonymize at 407, and register the data at 408 in the PAS database. At 409, the data can be formatted in a lighter format, such as Nifti, analyze. After formatting at 409, the data is ready to be treated by the selected quantifying algorithm 410. The results of the quantifying algorithm 410 can be used to produce the radiology report 412 that can be sent back to the PACS server 104.

In an example, as shown in FIG. 9, two quantifying solutions are listed in the estimator 303. The two quantifying solutions are the Automatic Ventricular Volume Estimator (AVVE) and the AHCE. As shown in FIG. 9, the flow path 501, between the filtered subjects 304 and flow work 502 (between PAS server 202 and PACS server 104) can be independent of the flow path 503, between the quantifying algorithm 410 and estimator 303. The flow path 501 can make the images available, while the flow path 503 can allow a user to select and implement quantifying tools so that PAS can solve, address, and/or detect a plurality of potential problems/diseases and at the same time add additional solutions using the same architecture.

Figure 10:
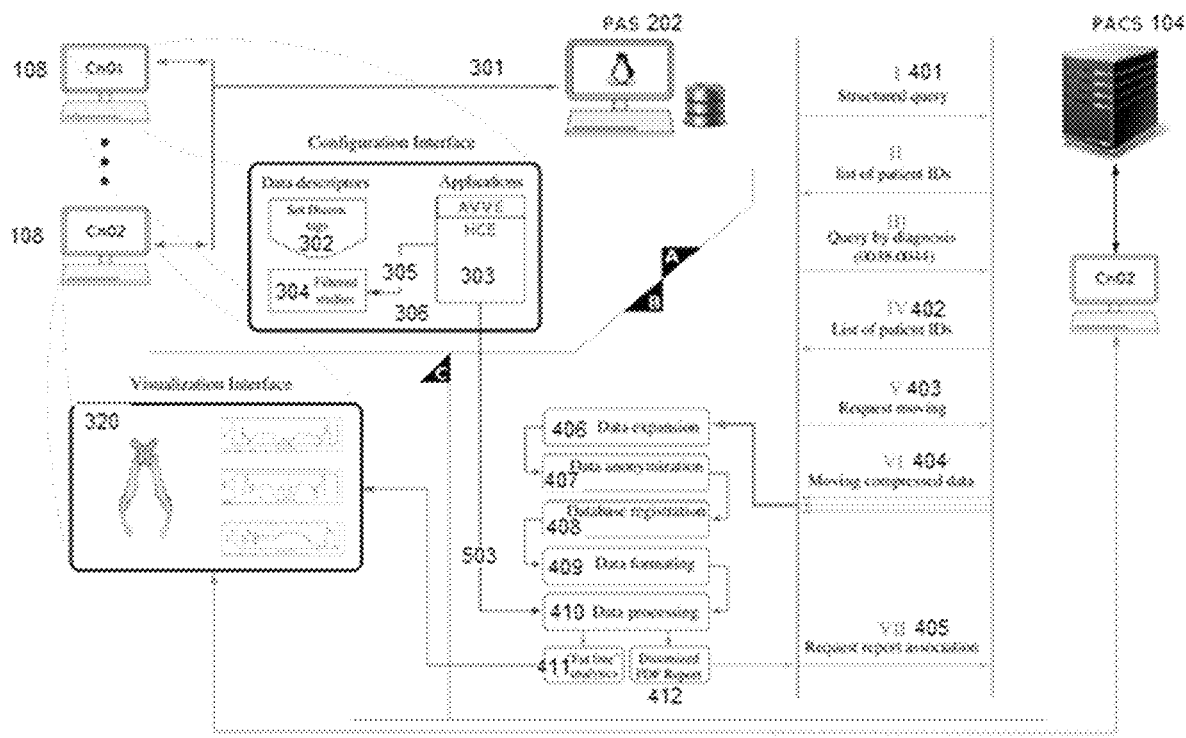
FIG. 10 illustrates the interactions and data flows of a PAS with a configuration interface and a visualization interface in an enhanced PACS system, according to an example of the present disclosure.

FIG. 10 illustrates the relationship of the configuration interface 306 and visualization interface 320 in an enhanced PACS-PAS system. Referring to FIG. 10, panel A corresponds to clients-PAS interactions and the PAS procedures listing, shown in FIG. 9. Panel B defines the set of messages interchanged between the PAS server 202 and PACS server 104 in a run without errors or exceptions, as shown in FIG. 6. Panel C illustrates the communication between the PACS visualizer PAS visualization interface 320 that can receive and automatically convert the extracted numbers of 411 from the numeric data collector 16 into a three-dimensional figure.

In operation, when a user logs in, a user field is set by default at 401. The application can then generate a request to the PAS, which will establish communication with the PACS to retrieve any requested data. The PAS can then automatically build searching strings that suit the conditions as defined by the user when associating the applications at 402. The PAS then retrieves the selected studies at 403 and moves the PACS complying data at 404 to decompression and decryption at 406, anonymization by removing the DICOM headers at 407, registered at 408, formatted at 409, and processed at 410, to create a desired report and/or a three-dimensional view of an image what is created by stacking several two-dimensional images. The data can then be processed as defined in the procedures box of the configuration interface 306. At the end of the processing stage, the resulting analytical information can be published in a PDF report, which is dicomized and send back to the PACS. By sending the dicomized report back to the PACS, a user can have access to the analytical information by a single click.

In an example, a permalink in the digital report activates the PAS visualization interface 320. Therefore, one additional click allows a user to interact with the analytical data in a JavaScript empowered in a web environment.

Still referring to FIG. 10, the programmatic pythonic tool can use a C-find instruction to retrieve headers as any other client would at 401 (I) and (II). However, the PAS will allow more interactions, such as by query by diagnosis as shown in (III) and (IV) 402 that provides bases for historical reports or population-based analysis. Accordingly, PAS can request PACS to provide the studies of interest.

The queries can be designed to find the accession numbers; thus, at the time when the images are requested to move 403 (V), the system only retrieves and moves the requested image and not all the patient associated images.

Furthermore, the PAS can also schedule this moving task during a low usage period of the network that is dynamically defined by ping-tests.

In operation, for example, a neurosurgery division that continually deals with quantifying ventricular volumes to diagnose and treat hydrocephalus may desire to compare the ventricular volume of a patient before and after the insertion or revision of cerebrospinal fluid (CSF) diverting shunt. The transaction storing needs in every processing stage is as shown in Table 2 below.

TABLE 2

Record of files' sizes and transactions executed by the AVVE algoritham for an in-house ventricular volume estimation. All file sizes in MegaBytes (MB)

| | DICOM | | Nifti | STL | Pdf | |
| --- | --- | --- | --- | --- | --- | --- |
| | Com-pressed | Expanded | (gz) | (bin) | Original | Dicomized |
| Before shunt | 5.49 | 14.23 | 5.33 | 1.81 | — | — |
| After shunt | 7.03 | 16.81 | 8.56 | 1.44 | — | — |
| Report | — | — | — | — | 1.00 | 1.01 |
| Total traffic | 12.52 | — | — | 3.25 | — | 1.01 |

The data needed to create this report occupies 12.52 MB of storage. From PACS to PAS, this data travels compressed and highly fragmented through the shared media in DICOM format. The received data was processed in the PAS, which in turn produces a quantitative report that used 1.01 MB of storing space. This report was moved back to PACS. At this point, the users have access to this report at their terminals. Additionally, a link was embedded in the report that provided access to the interactive environment, which was served by the PAS to any authorized client. To post this enriched-media information in a web browser, the PAS transferred 3.25 MB of data consisting of STL files embedded in JavaScript Object Notation (JSON) objects.

Figure 11:
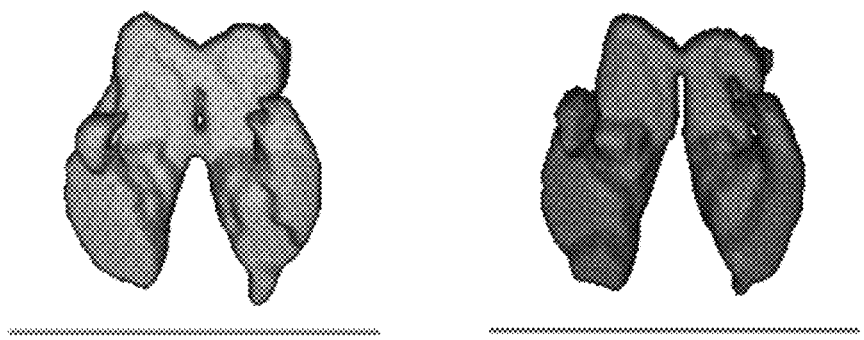
FIG. 11 illustrates a report showing ventricular change, according to an example of the present disclosure.

The final report is shown in FIG. 11. Additionally, the records of execution times of the tasks performed by the PACS-PAS vehicle, the data gathered while making the data of the before and after shunting framework available for AVVE processing is shown in Table 3 below.

TABLE 3

Records of execution times of the tasks performed by the PACS-PAS vehicle. The data is gathered while making the data of the before and after shunting framework available for AVVE processing.

| | | Data | |
| --- | --- | --- | --- |
| Step | Evaluation concept | Before | After |
| 1 | Listing studies per subject | 0.21 secs | |
| 2 | Obtaining SOPs | 0.04 secs | |
| 3 | Creating subject directory tree | 0.09 secs | |
| 4 | Retrieve data from PACS | 4.83 secs | 4.11 secs |
| 5 | decompressing and decrypting sintax file | 0.06 secs | 0.06 secs |
| 6 | decompressing and decrypting image data | 0.62 secs | 0.53 secs |
| 7 | Move data to nifti format | 2.86 secs | 2.33 secs |

Referring to Table 3 above, in the evaluation concepts 1 to 3, the activities performed are done for both datasets due to its common root, the patient. Also, after the retrieving actions are executed, the procedure does not involve any PACS-PAS transaction. After evaluation step 7, the data relating to the results of the analytical procedure can be accessible. However, to run another procedure, the system may need to retrieve the images again.

The before and after shunting data have 38 and 32 slices respectively. The differences in the amount of information are due to the different spatial resolution used during acquisition. The timings registered in Table 3 were obtained when running the procedures in a Dell server with an Intel four-cored i5 processor, using 16 GB in RAM and Ubuntu 14.04 64-bits operating system.

From the foregoing description, those skilled in the art can appreciate that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

The scope of this disclosure is to be broadly construed. It is intended that this disclosure disclose equivalents, means, systems, and methods to achieve the devices, activities and mechanical actions disclosed herein. For each device, article, method, mean, mechanical element or mechanism disclosed, it is intended that this disclosure also encompass in its disclosure and teaches equivalents, means, systems, and methods for practicing the many aspects, mechanisms and devices disclosed herein. Additionally, this disclosure regards a coating and its many aspects, features, and elements. Such a device can be dynamic in its use and operation, this disclosure is intended to encompass the equivalents, means, systems, and methods of the use of the device and/or article of manufacture and its many aspects consistent with the description and spirit of the operations and functions disclosed herein. The claims of this application are likewise to be broadly construed.

The description of the inventions herein in their many embodiments is merely exemplary in nature and, thus, variations that do not depart from the gist of the invention are intended to be within the scope of the invention. Such variations are not to be regarded as a departure from the spirit and scope of the invention.

We claim:

1. A system having patient image processing capability and being in compliance with health insurance portability and accountability act (HIPAA), the system comprising:
 a database; and
 a process application server communicatively connected to a picture archiving and communication system (PACS) server that stores medical data of patients in Digital Imaging and Communications in Medicine (DICOM) format, wherein the process application server is operated to:
  create a DICOM-complying structured query based on directives by a user for retrieving a specific set of patient medical images from the PACS server;
  transmit the DICOM-complying structured query to the PACS server, wherein, in response to the structured query;
  receive, from the PACS server, a list of matched service-object pairs (SOPs) that include the specific set of patient medical images;
  transmit, to the PACS server, a request to transfer the specific set of patient medical images;
  in response to the request to transfer, receive encrypted files of the specific set of patient medical images from the PACS server in a bulk manner and in compliance with confidentiality regulations of the HIPAA;

decrypt the encrypted files of the specific set of patient medical images;

anonymize the decrypted files of the specific set of patient medical images by removing personal information of the patients from the decrypted files;

register the anonymized files of the specific set of patient medical images in the database;

reformat the specific set of patient medical images in the registered files from the DICOM format into NIfTI or Analyze format;

operate a quantifying algorithm on the specific set of patient medical images in the NIfTI or Analyze format to generate numerical values representing areas, volumes, thicknesses, curvatures, depths, or roughness of features in the specific set of patient medical images;

analyze the numerical values representing the areas, volumes, thicknesses, curvatures, depths, or roughness of the features in the specific set of patient medical images to detect a pattern of abnormality in the specific set of patient medical images;

extract, from the numerical values, a set of numbers corresponding to the pattern of abnormality; and generate a report of the pattern of abnormality in the specific set of patient medical images using the extracted set of numbers.

2. The system of claim 1, wherein the process application server further anonymizes the decrypted files by removing DICOM headers in the specific set of patient medical images.

3. The system of claim 1, wherein, after detecting the pattern of abnormality in the patient medical images, the process application server assigns the pattern of abnormality to at least one of race, gender, socioeconomic status, completed studies, inheritance factors, preexisting medical conditions, cigarette and alcohol habits, and sport activities of owners of the patient medical images.

4. The system of claim 1, wherein, after detecting the pattern of abnormality in the patient medical images, the process application server assigns the pattern of abnormality to a geographical location where owners of the patient medical images reside, and determines at least one of a probability of an event and a cause of the pattern of abnormality.

5. The system of claim 1, wherein the process application server is further to:

perform medical services to owners of the patient medical images based on the pattern of abnormality.

6. A system communicatively connected to a picture archiving and communication system (PACS) server that stores medical data of patients in Digital Imaging and Communications in Medicine (DICOM) format, the system comprising:

a database;

a processor; and a non-transitory machine-readable storage medium storing machine-readable instructions that, when executed by the processor, cause the processor to:

create a DICOM-complying structured query based on directives by a user for retrieving a specific set of patient medical images from the PACS server;

transmit the DICOM-complying structured query to the PACS server, wherein, in response to the structured query;

receive, from the PACS server, a list of matched service-object pairs (SOPs) that include the specific set of patient medical images;

transmit, to the PACS server, a request to transfer the specific set of patient medical images;

in response to the request to transfer, receive encrypted files of the specific set of patient medical images from the PACS server in a bulk manner and in compliance with confidentiality regulations of the HIPAA;

decrypt the encrypted files of the specific set of patient medical images, anonymize the decrypted files of the specific set of patient medical images by removing personal information of the patients from the decrypted files;

register the anonymized files of the specific set of patient medical images in the database;

reformat the specific set of patient medical images in the registered files from the DICOM format into NIfTI or Analyze format;

operate a quantifying algorithm on the specific set of patient medical images in the NIfTI or Analyze format to generate numerical values representing areas, volumes, thicknesses, curvatures, depths, or roughness of features in the specific set of patient medical images;

analyze the numerical values representing the areas, volumes, thicknesses, curvatures, depths, or roughness of the features in the specific set of patient medical images to detect a pattern of abnormality in the specific set of patient medical images;

extract, from the numerical values, a set of numbers corresponding to the pattern of abnormality; and generate a report of the pattern of abnormality in the specific set of patient medical images using the extracted set of numbers.

\* \* \* \* \*